Figure 1:
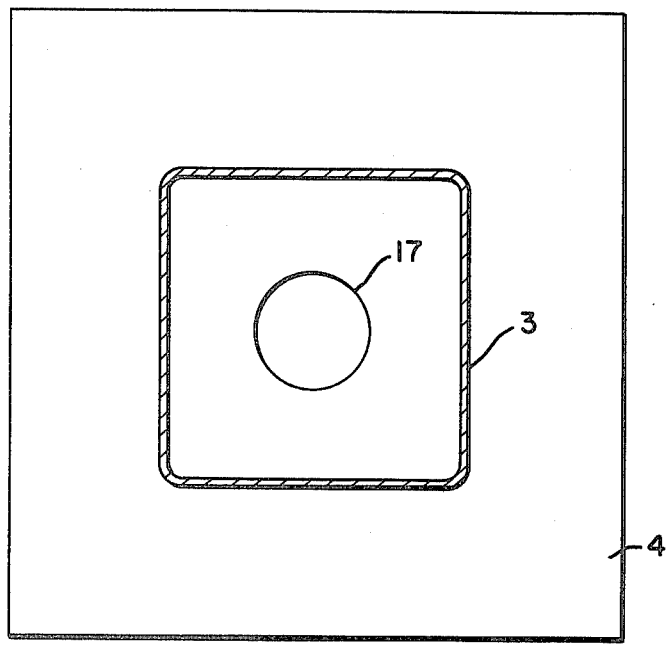

United States Patent [19]

Gereg

[11] Patent Number: 4,473,082
[45] Date of Patent: Sep. 25, 1984

[54] LUNG EXERCISER WITH VARIABLE RESISTANCE

[76] Inventor: Gordon A. Gereg, 159 Saw Pit Hill Rd., Woodbury, Conn. 06798

[21] Appl. No.: 275,590

[22] Filed: Jun. 19, 1981

Related U.S. Application Data

[63] Continuation-in-part of Ser. No. 199,084, Oct. 20, 1980, Pat. No. 4,345,605.

[51] Int. Cl.³ .................. A61B 5/08; A63B 23/00; F16J 3/00
[52] U.S. Cl. .................................... 128/728; 272/99; 92/43; 73/262; 128/205.17
[58] Field of Search ............... 128/727, 728, 205.16, 128/205.17, 725, 203.28, 730; 272/99 R; 92/43, 44; 73/262

[56] References Cited

U.S. PATENT DOCUMENTS

| | | | |
|---|---|---|---|
| 345,718 | 7/1886 | Munson | 128/728 |
| 513,924 | 1/1894 | Hartnett | 128/203.28 |
| 3,363,260 | 1/1968 | Garbe | 128/728 |
| 3,621,842 | 11/1971 | Manley | 128/205.16 |
| 3,754,546 | 8/1973 | Cooper | 128/727 |
| 3,810,461 | 5/1974 | McCormick | 272/99 |
| 4,096,855 | 6/1978 | Fleury, Jr. | 128/727 |
| 4,114,608 | 9/1978 | Russo | 128/725 |
| 4,241,740 | 12/1980 | Brown | 128/728 |
| 4,323,078 | 4/1982 | Heimlich | 128/728 |

FOREIGN PATENT DOCUMENTS

| | | | |
|---|---|---|---|
| 27154 | 4/1981 | European Pat. Off. | 128/728 |

*Primary Examiner*—Henry J. Recla

[57] ABSTRACT

A device consisting of an adjustable volume bellows made of inexpensive materials to be used as a visual indicator and volume measurement to encourage a patient to breath deeply as an exercise is provided. Means for adding calibrated weight to vary resistance is also provided.

2 Claims, 4 Drawing Figures

LUNG EXERCISER WITH VARIABLE RESISTANCE

RELATED APPLICATION

Gereg Ser. No. 199,084 filed Oct. 20, 1980 and now U.S. Pat. No. 4,345,605, for a lung exerciser, of which this is a continuation-in-part.

FIELD OF INVENTION

Surgery

OBJECTS

Patients with severe illness or those having been operated on recently are often too weak to the point where they find it difficult to breathe deeply. The human lung is a labyrinth of passages that get increasingly smaller deeper into the lung. If the small passages are not used at least occasionally over a period of time, they tend to clog and could atrophy. A normally healthy person will sigh or yawn on a fairly regular basis which exercises the small passages of the lungs. Deep breathing exercises or activities that require heavy breathing, such as running, are good for the lungs.

Since lung problems with inactive patients are a well known phenomenon, therapists have for some time used various devices to get the patient to use or redevelop their lungs. Among these are blow bottles which require a patient to blow water out of a bottle, ball type flowmeters which force a patient to draw or expire breath at a higher than normal rate, and volume related devices that measure the vital capacity of the lung and encourage deep breathing. There are also a number of positive pressure devices which force pressure into the lungs to expand them with the patient being passive.

The volume related devices that require a patient to inhale a set amount of air and repeat the exercise a number of times are currently the most popular. Generally they are a collapsible container with a calibrated, preset and adjustable volume that the patient must displace by inhaling 10 to 20 times a treatment. Bellows are commonly used as are folding bags and boxes. A collapsible container should fold easily with no build up or spring force as the patient empties it. Some bellows are so stiff that when the required volume is taken from them they have such a memory for their original shape that they create a negative pressure. More expensive or elaborate devices use counterweights or float a chamber in water to eliminate weight or negative pressure. Electronic devices coupled to flow meters can do the job very well.

What is proposed here is a simple, inexpensive device that can be readily understood and used and can be thrown away after one patient uses it. Materials used are common in both manufacturing and in hospital use. The design offers the therapist the opportunity to prescribe varied treatments to suit the patient. The basic bellows is very easy to empty since it is lightweight and a calibrated amount of weight can be added to offer a constant resistance.

When designing a disposable device it is important to use inexpensive materials and as little material as possible. It also must be possible to assemble the unit with a small amount of labor or machine time. A bellows to enclose a given volume (4 liters for example) could be made of rubber in a dip molding, or plastic in a blow molding. Welded bellows made of sheet plastic also can be used.

One of the cheapest ways to enclose a volume is with a plastic bag. Plastic such as polyethylene can be easily extruded into sheet or tubing and readily welded into a closed shape. If a series of sealed bags are stacked and sealed together near their center with interconnecting holes a bellows can be made.

If the volume of a bellows is known, a breathing tube or hose can be connected to it and a patient instructed to collapse the bellows by inhaling. It is best to have a stand to control the bellows and also to allow it to be adjustable as to volume.

Polyethylene bags with a thickness of 0.001 to 0.002 inch have adequate strength to hold positive or negative pressure in small amounts and are easily sealed to themselves or other materials. Other thicknesses may be used as well as other materials. When negative pressure is applied inside an expanded bellows made of thin polyethylene bags, the bellows tends to collapse from the sides rather than the bottom. The bellows should collapse from the bottom to make calibration practical. To prevent side collapse a series of cards (one in each layer) can be added. These cards (which may be cardboard or semi-rigid plastic) must be sized slightly smaller than the inside of the bag to allow the sides to come in a little when the bellows extends.

Some therapists are of the opinion that a small amount of weight added to the bottom of the bellows improves the therapy by offering a controlled resistance and causing the bellows to expand quickly after emptying. Since the amount of resistance needed is very controversial, it is an advantage to provide a unit where the resistance can be easily varied. In the present design, weight can be added in a pouch or bag provided at the bottom layer of the bellows and made as an integral part of the bellows although sealed off from the bellows. Since the bag or pouch can be airtight if a closure or reuseable seal is provided, it is quite convenient to use water as the weight. Other weights such as plates or balls of dense material can also be used.

The U-shaped support from which the bellows hangs can be made of inexpensive cardboard or rigid plastic. Graduations representing the volume of the bellows can be printed or labeled on the sides. If the support is sized to fit into a tray or box top and the tray can be slid up and down, the bellows can be volume sized for different patients.

If the U-shaped support is made of thin corrugated cardboard and the top card in the bellows also is, the output fitting can be snap fitted into a common hole in the two and used to hold the assembly together. Corrugated cardboard is easily scored and bent and can be folded nearly flat with the bellows collapsed inside. The bottom movable tray can be used to hold the collapsed assembly and with the addition of a box top or a cover sleeve, the assembly is packaged. The bottom box or tray can be made from a common box design that folds together. With the addition of two slots the box will work as the movable support. Either or both the box and the hanger could be made of other materials such as thermoformed plastic.

As with any exercise, counting the number of times the exercise is done is important. If the output connection is an elbow with a cleanout cap (making the elbow a tee) a means for getting to the moving bellows to sense the cycles is provided.

These and other objects will be apparent from the following specification and drawings in which:

FIG. 1 shows a plan view of the bag used as one layer of a bellows

Figure 2:
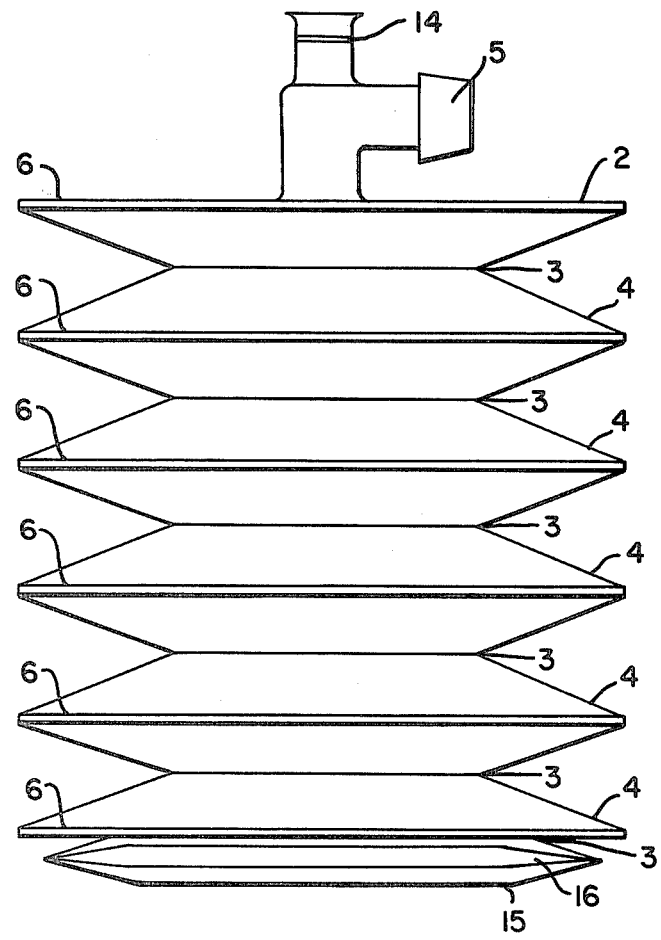
Figure 3:
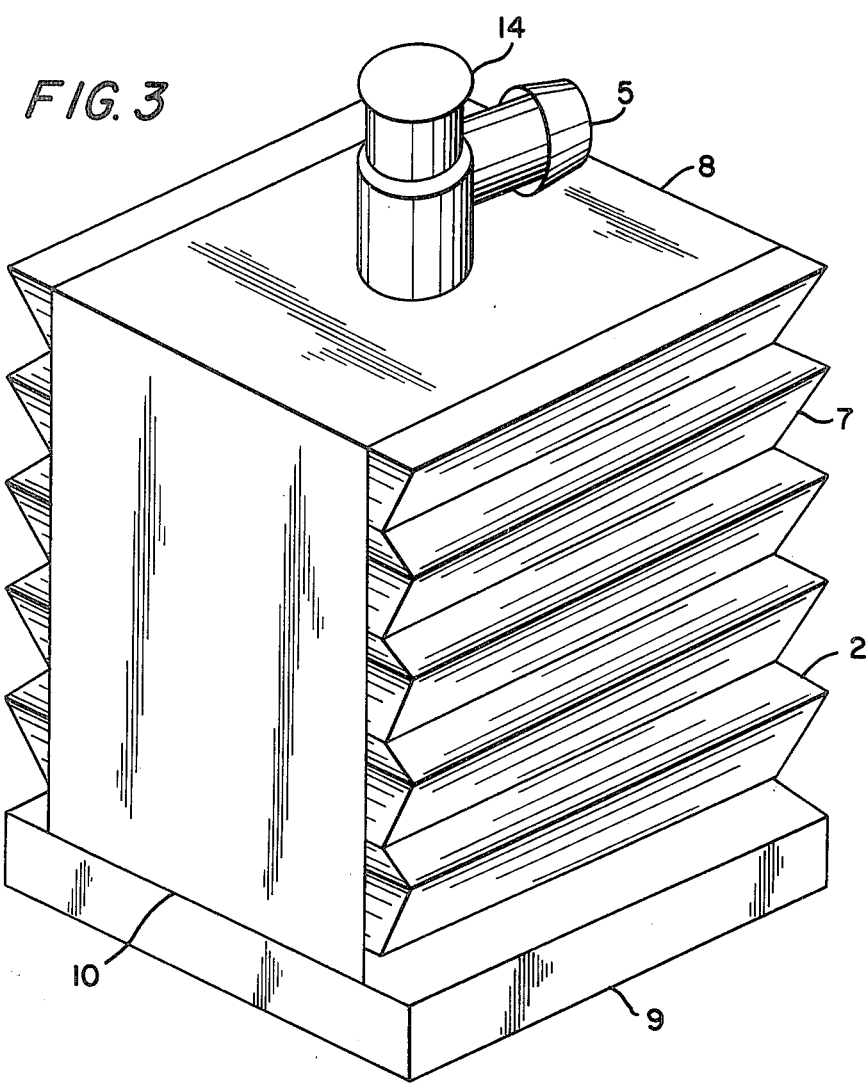
Figure 4:
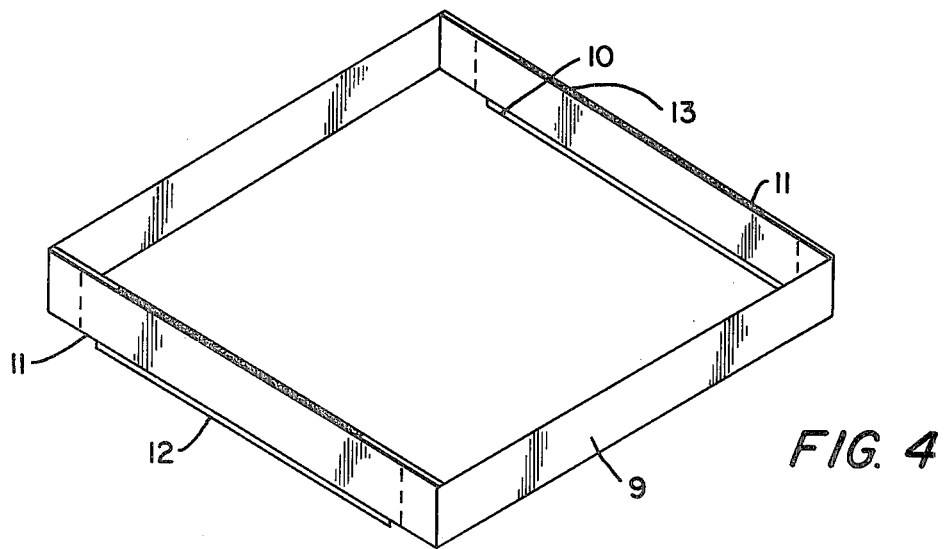

FIG. 2 shows a plan view of the bellows portion of the device including a pouch for weights FIG. 3 is a perspective view of the entire assembly FIG. 4 is a perspective view of the bottom tray of the device Referring now to the drawings, in which like reference numberals denote similar elements. FIG. 1 shows a bag 4 of the type commonly used in packaging and made of thin plastic such as polyethylene. The bag 4 as first manufactured is two layers of plastic closed on three sides either by welding three sides or using a sleeve welded on one end. A hole 17 is provided through both layers of plastic. A seal area 3 for assembly to another bag is shown and may take the form of a precut adhesive tape mounted on one side of bag 4. Glue could also be used as a joining means but the preferred approach would be a heat seal having the area and location 3.

FIG. 2 shows a bellows 2 formed by welding together a series of six plastic bags 4, said plastic bags being two sheets of plastic closed around all four outer edges. The weld in area 3 may be made by heat sealing, adhesive bonding or other suitable means and is shaped as a band around an unsealed area. Within the unsealed area a hole 17 is cut to interconnect the inner air space of each of the layers or bags 4. The interconnecting hole 17 shall be large enough to allow any air passed through top port 5 in either direction to move without restriction in volumes associated with breathing. A top fitting 5 of 22 mm diameter is a commonly accepted breathing tube connector. The top fitting 5 is attached to the top layer by suitable means such as heat sealing, adhesive bonding or by snap fitting into a flange ring or sheet provided inside the top bag. Each bag 4 when sealed on all four sides and to another bag 4 in weld area 3 becomes an element or layer of a bellows. Said bellows could be any number of layers suited to the end use.

Using the thinnest practical material for bags 4 to save cost will result in a bellows that is too flexible to withstand even a slight vacuum. Instead of the bottom of the bellows moving up and down, the sides will fold in. To prevent this, support cards or inserts 6 may be added. These cards are simple sheets of semi-rigid material such as cardboard, plastic sheet or heavy paper and are cut with a small clearance fit to the bag 4. Without a clearance the layers would be stretched tight when the bellows was folded and the bellows could not extend. The amount of clearance controls the maximum extension of the bellows.

Each card 6 except the lowest or bottom card should have a center hole at least as large as the hole between bellows 2 layers to allow free passage of air.

The weight of the cards 6 largely governs the action of the bellows 2 by providing the force that resists emptying the bellows 2. The cards 6 can be reduced in weight by using lightweight material such as foamed plastic, ribbed thin material or by using cutouts. There is little spring force in the bellows 2 which is a great advantage over other bellows designs since in combination with lightweight, it allows the resistance to emptying the bellows to be very low.

While very low emptying resistance is an important design criteria, being able to vary that resistance offers the therapist using the device another choice of treatment. In the present design it is quite easy to add another layer 15 that could be left open on the fourth side or provided with a resealable closure 16. This additional layer 15 would not have an interconnecting hole so it would be independent from the air space of the bellows 2. Being independent would allow the extra layer 15 to accept convenient material to add weight in any desired amount. If the closure 16 were water tight, water would make an ideally adjustable weight.

Given the bellows assembly 2 of FIG. 2, it is necessary to provide a means of hanging or supporting the bellows so it can be easily used. In FIG. 3 where the entire assembly is referenced generally by 7 the bellows assembly 2 is shown installed in a U-shaped hanger 8 and suspended by fitting 5. Hanger 8 could be made of semi-rigid material such as fluted cardboard or thin plastic. Fitting 5 has a suitable barb or fitting to allow it to be caught by a hole in hanger 8, and a similar hole in a card 6 inside bellows 2. Other assembly means such as adhesives could be used.

Hanger 8 is made narrower than bellows assembly 2 so that the bellows 2 is easily seen from any angle. By putting calibrations on the upright side of hanger 8, as the bellows 2 contracted, the bottom most layer would be used as an indicator of the volume left in the bellows or the volume displaced by the inhaler.

A tray 9 is shown at the bottom of assembly 7 which serves to hold the open end of the hanger 8 in place. The tray 9 has the form of a shallow box open on one side. The tray 9 would have slots 10 corresponding to the width of the legs of hanger 8 which would allow the tray 9 to be slid up and down the hanger 8 adjusting the volume limit of bellows assembly 2. This adjustment would be necessary to allow the therapist to adjust the treatment to the patient's needs. The closed side of tray 9 may be placed either up or down in the assembly depending on the volume or space needed.

The tray 9 could be a simple vacuum formed plastic box or preferably a folded cardboard box. Making cardboard boxes by die cutting, scoring and folding is commonly done. If the trap 9 is formed by folding a single sheet as shown in FIG. 4, two sides 11 are folded double thickness around two tabs tucked in from the remaining sides of the tray. Most often a slot 10 is provided in the bottom of the tray to accept a tab 12 sticking out of side 11 to allow the assembly to be locked together. In the present design the slots 10 are made somewhat wider in the narrow dimension so an extra layer of material could be slid through. A corresponding slot 13 is cut at the opposite edge of the fold on the open side of the tray so the leg of hanger 8 can slide all the way through.

Tray 9 is made large enough in all dimensions so the bellows 2 can be contracted, the legs of hanger 8 folded inward over each other and bellows 2 and the entire assembly 7 fitted into the tray. Since fitting 5 takes more height than the rest of the assembly 7, a space will be left into which accessories such as connecting tubing can be fitted. The entire assembly 7 of folded bellows 2 with hanger 8 in tray 9 can be covered with a sleeve, bag, or sheet of material to form a closed package.

Fitting 5 could be anchored firmly to bellows 2 or if it has a barb fitting and is snapped in, may be allowed to swivel. The swivel action would be a preferred feature. If an elbow shape is used for fitting 5, it would be easy to provide a port 14 at the bend that would be normally closed by a cap or plug. This passageway or port could be used to reach the inside of the bellows 2 particularly to the bottom layer so a counter or indicator could be provided to indicate the bellows had been completely emptied.

To make use of the device the therapist or patient would open the package and remove the hanger bellows assembly. The legs of hanger 8 should fall open and the bellows 2 extend itself. The legs of hanger 8 would be inserted through the slots 10 and 13 in tray 9. The choice of whether the open side of tray 9 was up or down would depend on the calibration or on the maximum volume desired. With the open side of tray 9 up towards the bellows, the maximum volume would be greater than the case with the closed side up by an amount proportional to the greater distance the bellows can travel. The tray would be positioned up or down on the hanger 8 to set the maximum volume desired for bellows 2 according to the calibrations provided on hanger 8.

The assembly 7 could be placed on its side with closure 16 open and facing upward. A predetermined amount of water could be poured into pouch 15 through closure 16 and closure 16 sealed. Alternately weight such as lead shot or metal sheets cut to fit pouch 15 could be used. After closure 16 in pouch 15 was closed the assembly 7 would be stood upright.

A breathing tube would be connected to fitting 5 so the patient could put the opposite end in his mouth (with the addition of a mouth piece) and communicate with the interior of bellows 2. To exercise, the patient would try by sucking air out of the breathing tube attached to the fitting 5, to empty the bellows completely. The therapist or physician would prescribe a number of times the exercise should be done and to what volume.

Accessories such as one way valves to insure rebreathing does not take place, a relief valve to limit vacuum, or a counter could be added at or around fitting 5 or in conjunction with the breathing tube or mouth piece.

I claim:

1. A device to provide exercise for a patient's lungs consisting of an adjustable volume bellows made of lightweight sheets of material such as plastic film in pairs, each pair of layers being stacked bonded in a thin line about the peripheral edge of each layer, each layer of each pair having a central small hole except for the bottom most layer, said bonded pairs then being bonded to another like pair at the periphery of said small hole provided at the center of each layer of adjacent layers the bottom most bellows layer which has no central hole is bonded to a pair of sheets bonded on three sides making an open pouch so a weight or heavy material may be added into the pouch and having the assembly of several layers of the bellows air tight and connected through said central holes and open only at said upper most layer through the center hole which hole is sized to pass breathing volumes of air in and out of the so formed bellows assembly and also provides a mounting hole an upper reinforcing layer of thin stiff material provided inside the upper most layer and having a small hole located at its center aligned with the central hole in said uppermost layer, a connector mounted in said mounting hole having one end sized to connect to breathing tubing and the other sized and shaped to be mounted and retained through said mounting hole and said holes in said upper reinforcing layer, additional reinforcing sheets having central holes also being provided between each layer of said pairs, said reinforcing sheets being sized to support the bellows to stop collapse under conditions of slight vacuum as occur when air is sucked out by a patient and also provide support when the so formed bellows assembly is fully extended in length, said reinforcing sheets being the limiting factor on how for a freely standing bellows could extend by limiting the inward motion of the four sides of each layer, a support hanger attached to said bellows assembly and having the shape of an inverted U, the bridge of said inverted U-shaped support being suspended from the connector and the legs extending along opposite sides of the bellows and being a length sufficient to support the bellows assembly fully extended, said legs being narrower than the bellows width to allow the bellows to be seen from all aspects, said support hanger also being collapsible to have each leg fold flat over the bellows when collapsed for storage, a storage box having one open side being large enough so the bellows assembly with support hanger could lay flat into the storage box, said box having opposite sides which are slotted the legs of the support hanger being passed through the slots making the assembly stable by holding the open side of the inverted U at any fixed location therealong and also allowing the storage box to be slid up or down the legs of the support hanger to adjust the maximum volume the bellows could be extended to thereby calibrating or prescribing the exercise treatment said legs adapted to be easily marked with calibrations according to the known volume of the bellows when extended to that point.

2. A bellows type lung exerciser as in claim 1, wherein said connector is rotatably mounted in said mounting hole.

* * * * *